(12) United States Patent
Semov et al.

(10) Patent No.: US 7,772,255 B2
(45) Date of Patent: Aug. 10, 2010

(54) METHOD OF TREATING TUMORS WITH AZAXANTHONES

(75) Inventors: Alexandre Semov, Dorval (CA); Grzegorz Pietrzynski, Montreal (CA); Valery Alakhov, Baie D'Urfe (CA)

(73) Assignee: Supratek Pharma, Inc., Dorval, Quebec (CA)

( * ) Notice: Subject to any disclaimer, the term of this patent is extended or adjusted under 35 U.S.C. 154(b) by 651 days.

(21) Appl. No.: 11/301,930

(22) Filed: Dec. 13, 2005

(65) Prior Publication Data

US 2007/0135473 A1     Jun. 14, 2007

(51) Int. Cl.
*A61K 31/44*     (2006.01)
(52) U.S. Cl. ...................................... 514/336
(58) Field of Classification Search ........................ None
See application file for complete search history.

(56) References Cited

U.S. PATENT DOCUMENTS

| 4,143,042 A | 3/1979 | Nohara et al. | |
|---|---|---|---|
| 6,552,055 B1 * | 4/2003 | Spiegelman et al. | 514/369 |

OTHER PUBLICATIONS

Gura et. al., Science, 1997, 278:1041-1042.*
Johnson et. al., British Journal of Cancer, 2001, 84:1424-1431.*
Wall M.E. and Wani M.C. Camptothecin and taxol: discovery to clinic—thirteenth Bruce F. Cain Memorial Award Lecture. Cancer Res. 1995 55, 753-760.
Kuczynski A. and Hill B.T. Vinflunine, the latest Vinca alkaloid in clinical development. A review of its preclinical anticancer properties. Crit. Rev. Oncol. Hematol. 2001 40, 159-73.
Bilenker J.H. et al. Phase I trial of combretastatin a-4 phosphate with carboplatin. Clinical Cancer Res. 2005 11, 1527-1533.
Meredith R.F. et al., Brief overview of preclinical and clinical studies in the development of intraperitoneal radioimmunotherapy for ovarian cancer. Clinical Cancer Res. 2007 13, 5643s-5645s.
Pang RW, Poon RT. From molecular biology to targeted therapies for hepatocellular carcinoma: the future is now. Oncology. 2007 72 Suppl 1 30-44.
Frese K.K, Tuveson D.A., Maximizing mouse cancer models. Nature Rev Cancer. 2007 7, 645-58.
Anisimov V.N. et al., Cancer in rodents: does it tell us about cancer in humans? Nat Rev Cancer. 2005 5, 807-19.
Paoloni M, Khanna C., Translation of new cancer treatments from pet dogs to humans. Nature Rev. Cancer. 2008 8, 147-56.
PCT Notification of Transmittal of the International Search Report and the Written Opinion of the International Search Authority or the Declaration dated Aug. 5, 2008.
PCT Written Opinion of the International Searching Authority dated Aug. 5, 2008.

* cited by examiner

*Primary Examiner*—Frederick Krass
*Assistant Examiner*—Marcos Sznaidman
(74) *Attorney, Agent, or Firm*—Porzio Bromberg & Newman, P.C.

(57) ABSTRACT

The use of azaxanthones for treating diseases associated with tumor cells which express one or more protein of S100 family, and in treating patients that have malignancies consisting of tumors of an epithelial or mesenchymel nature, where these compounds are effective in retarding the progression and/or metastasis of these tumors.

27 Claims, No Drawings

METHOD OF TREATING TUMORS WITH AZAXANTHONES

FIELD OF THE INVENTION

The use of azaxanthones for treating diseases associated with tumor cells which express one or more of the human S100 proteins.

BACKGROUND OF THE INVENTION

The S100 human proteins (S100A1, A2, A3, A4, A5, A6, A7, A8, A9, A10, A11, A12, A13, A14, A15, A16, S100B, S100P, S100Z) are a large family of cytoplasmic and extracellular Ca2+-binding proteins characterized by a high degree of conservation in amino acid sequence and 3-D structure [Zimmer, Sadosky and Weber (2003), Microsc Res Tech 60(6): 552-9]. They are small, acidic proteins of 10-12 kDa and contain two distinct EF-hands. A modified, S100-specific EF-hand is located at the N-terminus, followed by a classical Ca2+-binding EF-hand.

Neoplasias are the most numerous human diseases in which dramatic changes in the expression of S100 proteins occur. Over expression of S100A4, S100A6, S100A7, S100A11, S100A14, S100A16, S100B, S100P, or S100Z is common in many cancers of different origin (breast, colon, lung, pancreas, and others). At least partially such changes might be caused by rearrangements (amplifications) in chromosomal region 1q21, where most of S100 genes are clustered. Such rearrangements are frequently observed in different tumor cells.

Out of all S100 proteins the role for S100A4 in invasive growth and metastasis of cancers is especially well documented. Properties of this protein were recently reviewed in Helfman, Kim, et al. (2005) Br J Cancer 92(11):1955-8 and Mazzuchelli (2002) Am J Pathol 160(1): 7-13. Transfection experiments showed that S100A4 can induce a metastatic phenotype in previously non-metastatic rat mammary cells [Lloyd, Platt-Higgins, et al. (1998). Oncogene 17(4): 465-73], B16 murine melanoma cells [Parker, Whittaker, et al. (1994) DNA Cell Biol 13(10): 1021-8] and human breast cancer MCF-7 cells [Ambartsumian, Klingelhofer, et al. (2001) Oncogene 20(34): 4685-95]. Conversely, antisense S100A4 RNA or anti-S100A4 ribozyme suppressed the metastatic potential of highly metastatic cell lines [Maelandsmo, Hovig et al. (1996) Cancer Res 56(23): 5490-8 and Takenaga, Nakamura et al. (1997) J Cell Biol 124(5): 757-68]. The important role of S100A4 in tumor malignisation was demonstrated in transgenic mouse studies. It was shown that S100A4 by itself was not able to initiate tumors but it induced metastatic disease in originally non-metastatic tumors initiated by other oncogenes [Ambartsumian, Grigorian et al. (1996); Oncogene 13(8): 162 1-3 and Davies, Rudland et al. (1996); Oncogene 13(8): 1631-7]. When dynamics of tumor development were studied in S100A4 knock-out mice a significant delay in tumor uptake and decreased tumor incidences were observed. Moreover, tumors developed in S100A4(−/−) mice did not metastasize. Immunohistochemical analyses of these tumors revealed reduced vascularity and abnormal distribution of host-derived stroma cells. Coinjection of S100A4(+/+) fibroblasts partially restored the dynamics of tumor development and the ability to form metastasis, underlying the determinative role of host-derived S100A4-positive stroma cells in tumor progression and metastasis [Grum-Schwensen, Klingelhofer, et al. (2005) Cancer Res 65(9): 3772-80]. Altogether these observations suggest that S100A4 is not simply a marker for metastatic disease, but rather has a causal role in mediating this process.

The association between S100A4 expression and metastasis observed in animal studies has led to a number of studies examining the utility of S100A4 expression as a prognostic marker in human cancers. Two retrospective studies, based on the same well characterized group of 349 patients with a follow-up period of 19 years [Platt-Higgins, Renshaw, et al. (2000) Tnt J Cancer 89(2): 198-208; and Rudland, Platt-Higgins, et al. (2000), Cancer Res 60(6): 1595-603] analyzed the prognostic significance of protein S 100A4 in breast cancer and evaluated the association between protein expression, as detected by immunohistochemical staining, and variables with potential prognostic value for patient outcome. The antiserum stained 56% of the carcinomas either strongly or at a borderline level, whereas 44% of the carcinomas remained unstained. The overall survival for patients with carcinomas expressing S 100A4 was significantly worse than for those patients considered negative for S 100A4. In analogous studies the prognostic significance of protein S100A4 expression has recently been evaluated in a series of esophageal-squamous carcinomas, non-small lung cancers, and primary gastric cancers [Kimura, Endo et al. (2000) Tnt J Oncol 16(6): 1125-31; Yonemura, Bndou, et al. (2000) Clin Cancer Res 6(11): 4234-42; and Ninomiya, Ohta, et al. (2001) mt J Onco 18(4): 715-20]. Patients with S100A4-positive esophageal carcinomas [of 52 (25%)] had a significantly poorer prognosis than patients with S100A4-negative carcinomas; the protein S100A4 status in cancer specimens remained the only independent prognostic parameter in a multivariate analysis. Immunohistochemically S100A4 was detectable in 81 of 135 (60%) lung cancers. S 100A4 was found to be useful to identify patients with poor prognosis, as its tissue expression was correlated with progression of the tumor size as well as nodal status. Finally, protein S 100A4 was found to be significantly more expressed in poorly than in well-differentiated gastric adenocarcinomas [of 92 (55%)], and was correlated with nodal metastatic disease and peritoneal dissemination. Immunohistochemical studies revealed no staining for protein S 100A4 in the epithelial cells of normal colonic mucosa and in colonic adenomas, whereas carcinomas arising in adenomas and invasive carcinomas showed S100A4 expressing cells in 44% [of 18] and 94% [of 53] of cases, respectively (Takenaga, K., Y. Nakanishi et al. 1997). In pancreatic cancer, no S100A4 expression was found in low-grade intraepithelial neoplasia lesions [of 69], low level of expression was detected in high-grade pancreatic neoplasia lesions [of 18 (17%)], but most of pancreatic invasive carcinomas expressed S100A4 [of 61(93%)], see Rosty, Ueki et al. (2002) Am J Pathol 160(1): 45-50. Expression of S 100A4 was also associated with metastasis and poor survival in patients with bladder cancer [Davies, B. R., M. O'Donnell, et al. (2002) J Pathol 196(3): 292-9]. Altogether these results unequivocally demonstrate the importance of S100A4 protein expression for cancer progression, especially in the invasive stage.

SUMMARY OF THE INVENTION

In accordance with this inventory, it has been discovered that a compound of the formula:

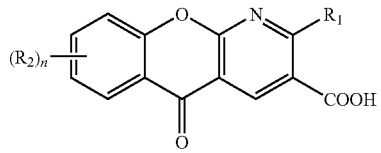

wherein R₁ is hydrogen, lower alkyl, phenyl, carboxyl, hydroxy, amino, mono-lower alkyl amino, or di-lower alkyl amino; R₂ is lower alkyl, lower alkoxy, halogen, nitro, hydroxy or carboxyl; and n is the integer 0, 1, or 2; or pharmacologically acceptable salts or esters thereof;

is effective in treating malignant or metastatic diseases associated with tumors which express a human S100 protein and therefore can be administered to humans to treat tumor cells which produce these proteins to retard the progression and/or metastasis of these tumors. In addition, it has been found that when these compounds are administered to patients that have malignancies consisting of tumors of an epithelial or mesenchymal nature, these compounds are effective in retarding the progression and/or metastasis of said tumors.

The invention also includes the novel meglumine salts of the compound of formula I and pharmaceutical compositions for administration which contain either the compound of Formula I in combination with meglumine or the meglumine salt of the compound of formula I. It is these meglumine salts which are present in the composition itself or form upon administration of the composition which enhance the effect of the compound of formula I in treating such tumors and retarding their progression. It the through the use of the meglumine salt that the compound of formula I can be administered effectively and efficiently at high dosages.

DETAILED DESCRIPTION

In accordance with this invention, the compounds of formula I, including their pharmacologically acceptable salts and esters are effective in treating the diseases associated with the expression of a S100 protein in tumor cells which produce these human S100 proteins. Therefore are useful in treating the various diseases, associated with tumors which express one or more human proteins of the S100 family. Those diseases associated with tumors which express this human protein include those malignant diseases resulting from tumors of the breast, skin, colon, lung, bladder, pancreas, esophagus, stomach or oral cavity. While these tumors result from tumor cells which produce one or more proteins of S100 family, the compounds of formula I including their pharmacologically acceptable salts and esters can be used in any other malignant disease resulting from said tumor cells which express these S100 proteins.

In accordance with this invention, the compound of formula I including its pharmacologically acceptable salts or esters can be utilized to treat malignancies in patients caused by tumors of an epithelial and/or mesenchymal nature by administering the compound of formula I, including its pharmacologically acceptable salts or esters, to such patients having these malignant tumors. The method of this invention can retard the progression and/or metastasis of any epithelial and or mesenchymal tumors. It has been found that through administration of the compound of formula I, which includes its pharmacologically acceptable salts or esters, the progression and/or metastasis of said tumors is reduced in the patient. In accordance with this method, progression of the tumor can be measured by the tumor size, total tumor burden and number of tumors in a patient treated in accordance with a claimed method. The effectiveness of the claimed method is determined by seeing if progression of the tumor is reduced by treatment in accordance with the claimed method as compared to patients not treated with the compound of formula I which includes its pharmacologically acceptable salts or esters.

Tumors progress in such a manner that they increase in size and in quantity in such cancer patients. Progression of the tumors can determined for example by measuring, during a given period, any increase in the size or quantity of the tumors, the tumor burden, appearance of secondary tumors or by any of the criteria of progression such as those set forth in the "WHO Handbook For Reporting The Results of Cancer Treatment, Geneva Switzerland World Health Organization Offset Publication No. 46:1979 and Reist Therasse Arbuck, et al., "New Guidelines to Evaluate the Response to Treatment in Solid Tumors;" Journal of the National Cancer Institute, Vol. 92, No. 3, Feb. 2, 2000.

However by treating the patient with the compounds of formula I, this progression and/or metastasis is reduced. However, the treatment of these patients with the compound of formula I as well as its pharmacologically acceptable salts or esters may not eliminate the initial tumor or reduce its size. Therefore, auxiliary therapy may be necessary to remove the primary tumor and the method of this invention can be used to prevent the further progression and/or metastasis of this primary tumor. Therefore, the method of this invention is especially adopted to be used as adjuvant therapy in connection with the removal and/or reduction in the size of the primary tumor.

The compounds of formula I are known compounds used as anti-allergic and bronchodilating agents as well as anti-inflammatory agents. See U.S. Pat. No. 4,143,042, Mar. 6, 1979 and U.S. Pat. No. 4,255,576, Mar. 10, 1981. However due to the limited solubility of these compounds, they have been difficult to administer, in either solid oral dosage forms or in liquid injectable dosage forms, especially at high dosages. The particularly preferred compound of formula I for use in this invention is amlexanox which is 2-amino-7-isopropyl-1-azaxanthone-3-carboxylic acid as well as its pharmacologically acceptable salts and esters. In fact, amlexanox is presently used commercially as a topical paste for treating canker sores such as aphthous ulcers in this regard amlexanox increases healing and decreases pain. In accordance with this invention, a new salt form of the compounds of formula I and in particular amlexanox is provided with enhanced solubility so that the compound of Formula I can be administered to human patients in either solid oral dosage forms or in liquid injectable dosage forms, especially at the high dosages for use in combating the progression and/or metastasis of epithelial and/or mesenchymal tumors in accordance with the methods of this invention.

The compound of formula I which are preferred are those compounds where $R_1$ is amino, i.e., a compound represented by the formula:

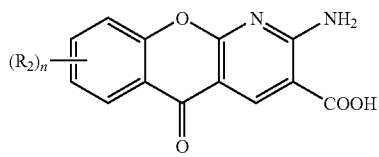

where $R_2$ and n are as above.

Besides amlexanox the other compounds of formula I-A which are especially preferred are 2-amino-7 chloro-1-azaxanthone-3-carboxylic acid and 2-amino-7,9-dimethyl-1-azaxanthone-3-carboxylic acid.

The compounds of formula I are relatively non-toxic and can be administered to human patients without danger of toxicity at high dosages. Among the other compounds of formula I which may be utilized in the process of this invention include:
1-azaxanthone-3-carboxylic acid;
2-amino-1-azaxanthone-3-carboxylic acid;
2-amino-7,9-dimethyl-1-azaxanthone-3-carboxylic acid;
2-amino-7-chloro-1-azaxanthone-3-carboxylic acid;
2-amino-7-ethyl-1-azaxanthone-3-carboxylic acid;
2-amino-7-isopropyl-1-azaxanthone-3-carboxylic acid;
2-amino-7-methoxy-1-azaxanthone-3-carboxylic acid;
2-amino-7-methyl-1-azaxanthone-3-carboxylic acid;
2-amino-7-n-butyl-1-azaxanthone-3-carboxylic acid;
2-amino-8-hydroxy-1-azaxanthone-3-carboxylic acid;
2-amino-g-methoxy-1-azaxanthone-3-carboxylic acid.

As used in the specifications, the term "lower alkyl", alone or in combination, means a monovalent straight or branched-chain saturated hydrocarbon alkyl group containing from one to six carbon atoms, such as methyl, ethyl, n-propyl, n-butyl, sec-butyl, isobutyl, tert-butyl, n-pentyl, n-hexyl or the like, with isopropoxy being especially preferred.

The term "lower alkoxy" means a straight-chain or branched-chain alkoxy group formed from lower alkyl containing from one to six carbon atoms, such as methoxy, ethoxy, n-propoxy, isopropoxy, n-butoxy, tert-butoxy and the like.

The term "lower alkylamino" designates amino substituents which are mono substituted or di-substituted with lower alkyl groups with lower alkyl being defined as above. In the case of the lower alkyl group substitution, the term "mono-lower alkyl amino" is used. In the case of two lower alkyl substituents on the nitrogen atom of the amine group, the substituent is a "di-lower alkyl amino group is used.

The term "pharmaceutically or pharmacologically acceptable salts" refers to conventional acid-addition salts that retain the biological effectiveness and properties of the compounds of formula I and are formed from suitable non-toxic organic and inorganic acids. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, methanesulfonic acid, oxallic acid, succinic acid, citric acid, malic acid, lactic acid, fumaric acid, and the like.

In addition to the acid addition salt, the compound of formula (I) can be used in the form of its basic salts such as corresponding organic amine salts, alkali metal salts or ammonium salts. These basic salts can be formed by reacting the compound of formula I in a conventional manner with an organic amine (e.g. ethanolamine, diethanolamine, triethanolamine, dl-methylephedrin, 1-(3,5 dihydroxyphenyl)-L-isopropylaminoethanol, isoproterenol, dextromethorphan, hetrazan (diethylcarbamazine), diethylamine, triethylamine, glucosamine, N-methylglucamine, etc.), an alkali metal hydroxide (e.g. sodium hydroxide, potassium hydroxide, etc.) or ammonia, for example for mixing them together and heating in a suitable solvent. The preferred salt for use in this invention is the novel N-methylglucamine salt [meglumine salt] which can be administered to the patient as a salt of the compound of formula I or in a mixture with the compound of formula I and the salt formed in situ upon administration of the mixture to the human patient.

The compound of formula I can be administered in the form of its pharmaceutically acceptable hydrolyzable esters. Any pharmaceutically acceptable hydrolyzable ester can be used in the compositions and methods of this invention. Among the esters are the aromatic esters such as benzyl (OBzl) or benzyl substituted with lower alkyl, halo nitro, thio, or substituted thio, i.e., lower alkyl, t-butyl, cyclopentyl, cyclohexyl, cycloheptyl, and 9-flourenylmethyl.

The compound of formula I is effective in treating tumors of an epithelial or mesenchymal nature. Such tumors include malignant or cancerous tumors of the breast, skin, colon, bladder, esophagus, stomach, larynx, lung or oral cavity, particularly the mouth.

In accordance with another embodiment of this invention, the compound of formula I is administered for treating patients who have had a treated malignancy resulting from tumors of an epithelial or mesenchymal nature or in conjunction with treating this malignancy. The administration of the compound of formula I to such patients inhibits both the recurrence of the treated malignancy and the progression and/or metastasis of this malignancy. The first malignancy which occurs in a patient may occur as cancer of the breast, colon, etc. and this primary malignancy may be treated by any conventional means of removal or reduction of the size, of the tumor such as by surgery, x-ray or other anti-tumor treatment or combination of thereof. In accordance with this embodiment of the invention, the administration of the compound of formula I provides adjuvant therapy to prevent spread of the first malignancy to a different site. Furthermore, the compound of formula I also retards or inhibits the development of a second malignancy. Hence, the compound of formula I may be utilized to prevent a second malignancy where the first primary malignancy is a carcinoma or tumor of the breast, skin, colon, bladder, esophagus, stomach, larynx, lung, mouth etc. after the first primary malignancy has been treated or in conjunction with treatment such as through surgery or other means of removal or reduction of the size of the tumor. In accordance with this invention, it is found that the compound of formula I is effective for preventing a recurrence of the primary malignancy and the development of a second primary malignancy where the first primary malignancy is, for example, a carcinoma of the breast. In using the compound of formula I for adjuvant therapy to prevent the development of a secondary primary malignancy or progression or metastasis of the primary tumor, the compound of formula I is administered in the same amount as described. Generally, it is preferred to administer the compound for use in adjuvant therapy orally as described above.

In accordance with a further embodiment of this invention, the compound of formula I can be utilized to treat carcinomas or tumors of mesenchymal or epithelial origin to retard the development and metastasis of these tumors. In accordance with the anti-carcinoma or anti-tumor properties of the compound of formula I, treatment of the tumors with the compound of formula I is especially effective in retarding the development of tumor of the breast, skin, colon, bladder, esophagus, stomach, larynx, lung or mouth. Among the carcinomas against which this compound is especially effective are carcinomas of the breast.

In the aforementioned treatments to retard the progression and/or metastasis of carcinomas of an epithelial or mesenchymal nature, as well as for preventing a recurrence of the primary malignancy and the development of a second primary malignancy, the compound of formula I is administered to patients affected by these carcinomas in an amount effective for retarding the progression and/or metastasis of these carcinomas or for preventing a recurrence of the primary malignancy or the development of a second primary malignancy. The amount will be dependent on the amount, type and size of the carcinomas and on the requirement of the patient. The dosage in the case of systemic administration varies in accordance with the requirements of the individual patient as determined by the treating physician. In general, the dosage in the case of systemic administration varies in accordance with the requirements of the individual patient as determined by the treating physician. In general, in administering the compound of formula I to such a patient, the compound of formula I is preferably administered orally at dosages of from about 3 mg to about 60 mg per kilogram of body weight of the patient per day. This dosage can be administered as a single dosage or in several divided dosages proportioned in accordance with the direction of a physician. In general, however, a daily oral dosage of about 5 mg to about 50 mg, preferably from about 10 mg to about 50 mg, per kilogram of body weight of the patient is generally preferred to be utilized. In accordance with the invention, the compound of formula I can be administered in solid oral unit dosage forms, such as capsules, tables, dragees, pills, powders, granulates and the like as well as liquid oral dosage forms such as solutions, syrups, suspensions, elixirs and the like. In general, the unit oral dosage forms should contain the compound of formula I in an amount of about 20 mg to 600 mg, preferably from about 30 to 500 mg and most preferably 30 to 300 mg. Of the unit oral dosage forms, capsules and tablets are especially preferred.

For the treatment given above, the compound of formula I is administered systemically as a composition containing the compound of formula I and a pharmaceutically acceptable carrier compatible with said compound. In preparing such composition, any conventional pharmaceutically acceptable carrier can be utilized. When the drug is administered orally, it is generally administered at regular intervals, conveniently at mealtimes or once daily. It has been established that the compound of formula I is relative non-toxic when given intravenously, intraperitoneally and when given orally.

The treatment of malignant tumors of epithelial and mesenchymal nature can be effected with the compound of formula I alone or in combination with other measures for reducing the size or eliminating the tumor. Any conventional means for reducing the size or eliminating the tumor can be used in conjunction with the method of this invention. These include surgery, radiation therapy, hormone therapy or treatment with standard chemotherapy (cytostatics and cytotoxins) or other biological response modifies (including antibodies and their derivative molecules, interferons, interleukins, or other lymphokines)

As administration forms for systemic administration there are the usual solid or liquid dosage forms, e.g. suppositories or as solid oral dosage forms capsules, tables, dragees, pills, powders, granulates and the like, as liquid oral dosage forms solutions, syrups, suspension, elixirs and the like and as parenteral dosage forms for infusion or injection solutions which can be injected intravenously or intramuscularly.

The compounds of Formula I can be also be administered parenterally by injection. Any conventional means of injections such as i.v or i.p. can be used for administering the compounds of formula I or its pharmacologically acceptable esters or salts. These injectable forms can be formed with sterile aqueous solutions of this compound in conjunction with standard additives utilized in such injectable forms.

In accordance with this invention we have found the dosage for parenteral administration for injection is the same as for the oral dosage forms, i.e., from about 3 mg to about 60 mg per kilogram of body weight of the patient per day. This dosage can be administered as a single dosage or in several divided dosages proportioned in accordance with the direction of a physician. In general, however, a daily injectable dosage of about 5 mg to about 50 mg, preferably from about 10 mg to about 50 mg, per kilogram of body weight of the patient is generally preferred to be utilized. With respect to these injectable dosages, the compound of formula I is a solution. This solution generally contains from about 2 mg/mL to about 20 mg/mL of the compound of formula I. The unit injectable dose can be in a amount of from 5 mL to 1000 mL of solution containing the aforementioned amount of the compound of formula I.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Chemical stabilization of the compound of formula I, its salts and its solutions may require addition of certain antioxidants into its formulation. Various antioxidants are commonly used for chemical stabilization. It is preferred that antioxidant used is ascorbic acid, or its pharmaceutically acceptable salts.

In accordance with this invention it is found that unexpected results are achieved through the use of the compound of formula I as its salt with N-methylglucamine (meglumine). The use of these meglumine salts makes the compound of formula I, which is only sparingly soluble in water, soluble so that it can be administered in high dosages to obtain the beneficial effects to treat tumors of the mesenchymal or epithelial origin, to retard the development and the metastasis of these tumors and to prevent the recurrence of a primary malignancy or the development of a secondary primary malignancy. In accordance with an embodiment of this invention the compound of formula I can be administered as the meglumine salt. This can be done by providing the meglumine salt of the compound of Formula I in the dosage form to be administered or by providing a solid oral unit dosage form containing a combination of meglumine with the compound of Formula I as a free acid or in another salt form. This combination when mixed with water or when administered to the patient will form the meglumine salt so that the meglumine salt will be administered to the patient. Therefore by means of providing a mixture of the compound of formula I and meglumine in the oral unit dosage form the meglumine salt will be administered to the patient. On the other hand, when the mixture of meglumine and the compound of formula I as a free base is added to the liquid injectable unit dosage form, the meglumine salt of the compound of formula I is formed in this injectable dosage form. In this manner, the enhanced soluble form of the compound of formula I can be administered parenterally to the human patient.

In forming oral unit dosage forms containing meglumine and the compound of formula, the unit dosage form contains at least 0.5 parts by weight of meglumine per part by weight of the compound of formula I. While higher amounts of meglumine, i.e., above 0.5 parts by weight based upon the weight of the compound of formula I, can be utilized in the composition of the oral unit dosage form, it is preferred to utilize no more than about 1.2 parts by weight of meglumine per part by weight of the compound of formula I in these compositions since the provision of such excess amounts of meglumine may raise the pH of the dosage form to levels too high to be adminstered to patients. Generally from about 0.5 to 0.8 parts be weight of meglumine per part by weight of the compound of Formula I are present in the oral and injectable compositions. On the other hand, salts other than meglumine can be utilized in these compositions. However, for best results, it has been discovered that the use of meglumine in these compositions, to form the meglumine salt of the compound of formula I are especially advantageous.

The following examples are provided to illustrate the invention utilizing the compounds of Formula I are not to be construed as limiting the invention. In the examples the parts by weight of ingredients in a composition is given based upon the total weight of the composition. In the tables which appear in certain of the examples, such as in Example 13, the compositions prepared are designated by F numbers such as F1. This is used to refer to the particular composition given in this table.

In the tables given in the following examples the main pharmacokietic parameters of amlexanox and bioavailablility of amlexanox salt and acid are set forth using the following abbreviations:

AUC area under the concentration-time curve $C_{max}$ maximum concentration $t_{1/2}$ elimination half life MRT mean residence time CL clearance $V_{SS}$ volume of distribution steady state In the examples Pruve is sodium stearyl fumarate.

EXAMPLES

Example 1

Amlexanox 20 mg Tablets 400 mg of 2-amino-7-isopropyl-1-azaxanthone-3-carboxylic acid, 590 mg corn starch and 10 mg magnesium stearate were mixed for 60 minutes in a planetary mixer to produce a 1000 mg of a mixture. Each tablet was prepared by charging 50 mg of this mixture into a dye (diameter 7 mm), and were pressed into a tablet using surface pressure of about 10000 N/cm$^2$. This produced individual tablets containing 20 mg of amlexanox.

Example 2

Amlexanox Injectable Dosing Solution 20 mg/mL 20 mg of 2-amino-7-isopropyl-1-azaxanthone-3-carboxylic acid sodium salt was dissolved in 1 mL of 0.9% sterile aqueous sodium chloride solution for infusion, prior to administration. Alternatively, 20 mg of 2-amino-7-isopropyl-1-azaxanthone-3-carboxylic acid sodium salt was dissolved in 1 mL of 5% sterile aqueous dextrose solution for infusion, prior to administration.

Example 3

Amlexanox 250 mg Tablets 500 mg of 2-amino-7-isopropyl-1-azaxanthone-3-carboxylic acid, 490 mg corn starch and 10 mg magnesium stearate were mixed for 60 minutes in a planetary mixer to produce 1000 mg of a mixture. Each tablet was prepared by charging 500 mg of the mixture into a dye (diameter 13 mm), the tablets containing 250 mg of 2-amino-7-isopropyl-1-azaxanthone-3-carboxylic acid and were pressed using surface pressure of about 10000 N/cm$^2$.

Example 4

Amlexanox Injectable Dosing Solution 10 mg/mL 500 mg of 2-amino-7-isopropyl-1-azaxanthone-3-carboxylic acid sodium salt was dissolved in 50 mL of 0.9% sterile aqueous sodium chloride solution for infusion, prior to administration.

To achieve the dose 500 mg, 50 mL of the solution is administered to the subject by intravenous infusion.

Example 5

Preparation of Water-Soluble Amlexanox Sodium Salt

Amlexanox was solubilized in NaOH, pH of solution was adjusted to 7.6-7.8 with 1 M Tris, pH 7.4 and desirable volume was adjusted with autoclaved distilled water. Final concentration of NaOH was equimolar to concentration of amlexanox. Specifically, to make 20 ml of 20 mg/ml amlexanox solution, 400 mg of amlexanox were dissolved in 10 ml of 132 mM NaOH and then 5.2 ml of 1 M Tris, pH 7.4 and 4.8 ml of water were added. Solution of amlexanox was sterilized through 0.2 micrometer filter. Measurement of intrinsic amlexanox fluorescence confirmed that there was no loss of amlexanox during filtration.

Example 6

Amlexanox Inhibits Metastasis Formation by S100A4 Positive Cells in Animal Model The Amlexanox injection solution prepared as described in Example 4. Highly metastatic S 100A4-positive CSML100 cells (Ret) were inoculated intravenously in groups of female A/J mice (6-7 week old, n=26) obtained from the Jackson Laboratory (Maine, USA). The animals were then divided randomly into the following two groups: 1) intact control (n=16, treated saline) and 2) Amlexanox (n=10, 100 mg/kg, injected i.v. daily for 10 days). In both groups the injection volume was 5 ml/kg. The treatments were started from the day following the tumor cell implantation for 10 consecutive days. The animal body weight was recorded as an index of treatment toxicity during the experiment.

Starting from the day 10 after the cell implantation, one animal of the control group was sacrificed every day to monitor the metastasis development. All animals were sacrificed on day 18 for routine metastasis inspection. Although all organs were routinely screened, metastatic formation was only found in the lung. The metastatic colonies on the organ surface were enumerated immediately following the removal of the organ.

The data were expressed as mean±SEM for the number of metastatic sites. The results of the experiment are presented as follows:

| Animal group | Average of lung metastasis number per animal | Trial/control × 100% |
|---|---|---|
| Control | 38.8 ± 7.3 | 48.5% |
| Amlexanox | 18.8 ± 2.3 | |

Amlexanox produced significant inhibition on metastases formation in the mice inoculated CSML100 cells. A non-significant body weight loss of less than 10% was detected in the Amlexanox treated group indicating a low or no toxicity of the treatment.

Example 7

This study demonstrates the efficacy of treatment with amlexanox in women breast cancer patients whose primary tumors are removed surgically. In this study, 44 women with metastatic (Stage III-IV) breast cancer whose primary tumors are removed surgically are treated by orally administering 500 mg amlexanox twice a day. The total dose, per patient, is 1,000 mg daily. Baseline assessments are performed at the start of the treatment (treated group) and these baseline results are compared with repeat assessments during various follow-up periods of this treatment. The treatment is conducted for at least ten consecutive days and it is continued further until substantial progression of the disease is noted. The study, which includes treatment of all patients and their follow-up, lasts for at least nine months or until disease progression in the last patient with responding or stable disease. The primary purpose of the study is to determine in the treated women the overall (complete and partial) response rate during treatment and the follow up period. The study is also carried out to determine the time of delay to disease progression of each of the patients in the treated group. Definitions of complete and partial response, stable disease (neither response nor progression), time to progression are the standard definitions according to the WHO and/or RECIST criteria that are routinely used in cancer treatment trials. In carrying out this study, the response rate and one year survival data for each of the patients in the treated group is determined and compared with an untreated group.

Patients receive 500 mg of amlexanox, twice daily, by administering two 250 mg tablets, prepared in Example 3, twice daily for at least 10 consecutive days. Treatment is stopped in a patient when there is no delay of substantial progression of the disease after the initial 10 day period. If there is a delay of the substantial progression of the disease, then treatment is stopped when it is determined that substantial progression of the disease in that patient resumes. However, the entire study is carried out for at least nine months after the last patient with stable or responding disease entered the study or until the disease has progressed in all of the patients. Patient assessments are carried out every fourteen to forty-two days during the study with the first follow-up assessments taking place fourteen days after first administration of the amlexanox tablets. Tumor assessments are carried out at least every forty-two days from the start of treatment.

The following baseline assessments in each of the patients are made [the "Baseline Assessments"]: demographic data, medical history, complete physical exam, height and weight, vital signs, Karnofsky performance status, hematology, blood chemistry and urinalysis. Pregnancy tests in women of childbearing potential are also performed within 48 hours. The Baseline Assessment of the tumor includes a chest and abdominal CAT scan for all patients and a bone scan for patients who had an abnormal scan 3 months prior to study entry.

During treatment with amlexanox the following assessments are made every fourteen to forty-two days: physical exam, weight, performance status, vital signs, hematology, blood chemistry and urinalysis. A clinical assessment including adverse event review, concomitant medication and concurrent illness are also done. One week after the first administration of amlexanox, patients are clinically evaluated (adverse event review, concomitant medication and concurrent illness) and the following laboratory evaluations are conducted: hematology, blood chemistry and urinalysis. Tumor assessment is performed every six weeks during and every three months after treatment until progression is confirmed by standard WHO and/or RECIST criteria.

After completion of treatment with amlexanox patients are seen one week after the last treatment with amlexanox and the following tests completed: physical exam, weight, performance status, vital signs, chest X-ray, hematology, blood chemistry and urinalysis. A clinical assessment including adverse event review, concomitant medication and concurrent illness are also done.

After completion of study treatment or after early withdrawal from study treatment, in order to address survival, patients are followed every three months for up to twelve months or until death if it occurs earlier. Parameters assessed are: physical exam, weight, performance status and vital signs. A clinical assessment including adverse event review, concomitant medication and concurrent illness are done, as well as tumor assessments in patients without progression of their disease by standard WHO and/or RECIST criteria.

Patients discontinued from the study for any reason come for a study termination visit. Parameters assessed are: physical exam, weight, performance status, vital signs, chest X-ray, hematology, blood chemistry and urinalysis. A clinical assessment including adverse event review, concomitant medication and concurrent illness are also done, as well as tumor assessment in patients without progression of their disease by standard WHO and/or RECIST criteria.

The primary efficacy variables are the overall response rate and time to disease progression. To evaluate the overall response rate, two sets of analyses are performed, one based on the intent to treat (ITT) approach (all eligible patients) and one based on data from evaluable patients only, i.e. all eligible patients who complete at least one course of therapy and undergo tumor evaluation. Time to disease progression is defined as time from the beginning of treatment until documented disease progression by standard WHO and/or RECIST criteria. This analysis includes all eligible patients from the ITT population who received at lease one dose of amlexanox.

Duration of overall response is measured from the time measurement criteria are met for CR or PR (whichever status is recorded first) until the first date that recurrence or PD is objectively documented, taking as reference for PD the smallest measurements recorded since the treatment started. All patients are followed for survival, which is measured from the beginning of amlexanox therapy for a period of one year or until death whichever occurs first. All patients who receive at least one dose of amlexanox are included in the safety analysis. Any incidence of adverse events are recorded and classified according to body region and toxicity grade. Clinically significant laboratory data is tabulated.

All of the patients during the evaluation period are evaluated for the measurement of the tumors, survival and determination of any progression of the disease in the patient. Stability is measured during each evaluation to determine if there is any increase in the size and amount of tumors from the proceeding period and if there is no subsequent appearance of any other malignancies in the patient. Clinically significant laboratory data is tabulated.

Based upon the results, at the end of the study, it is predicted that a greater percentage of the patients in the group of patients treated with the amlexanox show little or no progression of the disease which is calculated from the base line period until the termination of the study nine months after administration of amlexanox and follow-up as compared to the non-treated group.

Example 8

This is a study to demonstrate the effectiveness of amlexanox as a monotherapy in treating patients with advanced metastatic breast cancer resistant to prior chemotherapy including anthracyclines and/or taxanes.

In this study 44 women patients with metastatic (Stage III-Stage IV) breast cancer who have relapsed following prior cytotoxic chemotherapy regiments containing anthracyclines and/or taxanes are treated by administering 500 mg amlexanox twice daily with two amlexanox 250 mg tablets prepared in Example 3 taken twice daily orally as outpatients. This treatment is carried out for determining the overall (complete and partial) response rate. In this group, the stable disease rate of patients treated with amlexanox is determined. In addition, in each of the treated patients, the time to disease progression is also determined. The results of this study are compared to untreated patients with metastatic (Stage III-Stage IV) breast cancer who have relapsed following the same prior cytotoxic chemotherapy regiment.

In this study, each of the patients are treated twice daily with two 250 mg amlexanox tablets (prepared in Example 3) taken orally twice daily on an outpatient basis to provide a daily dose of 1000 mg per patient. The duration of treatment is initially for at least six weeks. The patients are evaluated by standard WHO and/or RECIST criteria for response and disease status at six week intervals. The patients who respond (complete or partial response) or have stable disease at the end of six weeks of treatment continue to receive treatment until progression of the disease is observed. A patient documented with disease progression is removed from the study. The patients with complete or partial response and patients with stable disease are treated until substantial disease progression, or if longer, until the end of this study or until early withdrawal from study. In order to address survival, patients are followed up every 12 weeks after withdrawal from the study. This study ends after nine months of treatment with follow up of the last non-progression patient.

All of the patients receive a Baseline Evaluation as set forth In Example 7 and the progression of the disease and the patient evaluation during treatment and follow up are carried out as described in Example 7. All of the patients during the evaluation period are evaluated by the measurement of the tumors, survival and determination of any progression of the disease in the patient. Stability is measured during each evaluation to determine if there is any increase in the size and amount of tumors from the proceeding period and if there is no subsequent appearance of any other malignancies in the patient. Clinically significant laboratory data is tabulated.

Based upon the results, at the end of the study, it is predicted that a greater percentage of the patients in the group of patients treated with the amlexanox show no progression of the disease by standard WHO and/or RECIST criteria which is calculated from the base line period until the termination of the study nine months after administration of amlexanox and follow up as compared to the non-treated group.

Example 9

This is a study to demonstrate the effectiveness of amlexanox in combination with irinotecan in treating patients with colorectal cancer as a first-line therapy.

In this open label randomized multicenter study 150 patients with colorectal cancer who have tumors that cannot be completely removed by surgery are treated by administering irinotecan alone and 150 patients, with colorectal cancer who have tumors that cannot be completely removed by surgery, are treated with combination of irinotecan and 500 mg amlexanox daily with two amlexanox 250 mg tablets, prepared in Example 3, taken twice daily orally to provide a daily dose of 500 mg of amlexanox. Irinotecan was administered to all of the patients at a dose of 350 mg/m$^2$ once every 3 weeks intravenously during the course of this study. At participating treatment centers every patient receives all treatments considered standard of care including chemotherapy with irinotecan. Patients who have histologically proven advanced colorectal cancer; not amenable to curative surgery, are included in the study. Patients who received no previous chemotherapy for metastatic disease are eligible, but prior adjuvant therapy is permissible. In case of a single metastasis, histological or cytological proof of colorectal carcinoma is obtained prior to randomization. In case of previous radiotherapy, at least one measurable lesion is located outside the irradiated field. This treatment is carried out for determining the overall (complete and partial) response rate as a primary endpoint. In addition, in each of the treated patients, duration of overall response, time to overall response, duration of progression-free survival, overall clinical benefit rate, overall survival rate and quality of life are determined. The results of this study are compared between two groups of patients.

The duration of amlexanox treatment is initially for at least six weeks. The patients are evaluated by standard WHO and/or RECIST criteria for response and disease status at six week intervals. Patients who respond (complete or partial response) or have stable disease at the end of six weeks of treatment continue to receive treatment until progression of the disease is observed. Patients documented with disease progression may be removed from the study. The patients with complete or partial response and patients with stable disease are treated until substantial disease progression, or if longer, until the end of this study or until early withdrawal from study. In order to address survival, patients are followed up every 12 weeks after withdrawal from the study. This study ends after nine months of treatment with follow up of the last non-progression patient.

All patients receive a baseline evaluation as set forth in Example 7 and the progression of the disease and the patient evaluation during treatment and follow up are carried out as described in Example 7. All of the patients during the evaluation period are evaluated by the measurement of the tumors, survival and determination of any progression of the disease in the patient. Stability is measured during each evaluation to determine if there is any increase in the size and amount of tumors from the proceeding period and if there is no subsequent appearance of any other malignancies in the patient. Clinically significant laboratory data is tabulated.

Based upon the results, at the end of the study, it is predicted that a greater percentage of the patients in the group of patients treated with the amlexanox show beneficial results including, but not limited to, at least one of the following endpoints: overall response rate, duration of overall response, time to overall response, duration of progression-free survival, overall clinical benefit rate, overall survival rate and quality of life.

Example 10

Preparation of Crystalline Amlexanox Sodium Salt 1 g of amlexanox was accurately weighed and added to 7 ml of water. The suspension was stirred for 10 minutes. To this suspension 3 ml of 1.0N NaOH was added slowly. The suspension was stirred until the amlexanox was fully dissolved. The pH of the clear solution was adjusted to 7.4 by adding solid amlexanox, and diluted to 10 mL by adding water. The excess of amlexanox was removed by filtration. 400 mL of isopropanol was added slowly while the mixture was vigorously stirred. First crystals of sodium salt appeared while mixture was stirred, and crystallization was complete within 2 hours. The crystalline product was separated by filtration and dried in vacuum.

Example 11

Preparation of Crystalline Amlexanox Magnesium Salt and Crystalline Amlexanox Calcium Salt 0.001 mol of Amlexanox sodium salt was dissolved in 30 mL of water, and 0.0005 mol of magnesium chloride was dissolved in 30 mL of water. The solutions were mixed slowly with stirring. Resulting precipitate was filtered off, washed with 100 mL of water and dried.

The same procedure using calcium chloride instead of magnesium chloride was used to prepare crystalline amlexanox calcium salt.

Example 12

Preparation of Instantly Soluble Amlexanox Formulation with Meglumine

The compositions of instantly soluble amlexanox formulations with meglumine are listed in the Table below. The compositions were prepared by mixing of weighted amounts of dry powders for 90 minutes in a planetary mixer. Dissolution of the formulation was tested by placing the 85 mg of powder formulation in 5 mL water. The solution becomes clear in less than 2 minutes.

| Formulation | Amlexanox [mg] | Meglumine [mg] | Maltol [mg] | Ascorbic acid [mg] | Propyl galate [mg] | Strawberry flavor* [mg] |
|---|---|---|---|---|---|---|
| F1 oral and for injection | 1000 | 687 | — | — | — | — |
| F2 for injection | 1000 | 687 | — | 6 | — | — |
| F3 oral | 1000 | 687 | 4.2 | — | — | 5 |
| F4 oral | 1000 | 687 | — | 6 | — | 5 |
| F5 oral | 1000 | 687 | — | — | 7.1 | 5 |

Example 13

Preparation of Amlexanox Tablets

The compositions of the tablets are listed in the Table below. The prescribed amounts of Amlexanox, and the prescribed amounts of the excipients, in milligrams, were mixed in a planetary mixer for 60 minutes. The 20 mg and 100 mg strong tablets were prepared using a 7 mm dye. The 250 mg tablets were prepared using 13 mm dye. The tablets were pressed with 5000 lb pressure using Carver Hydraulic Laboratory Press.

| Name | Amlexanox parts by weight | Corn starch parts by weight | Pruve parts by weight | Carbopol 971P parts by weight | Meglumine parts by weight | Cellulose crys. parts by weight | Lactose parts by weight | Tablet weight (mg) |
|---|---|---|---|---|---|---|---|---|
| Amlexanox 20 mg | 400 | 590 | 10 | — | | — | — | 50 |
| Amlexanox 250 mg | 5000 | 4900 | 100 | — | | — | — | 500 |
| Amlexanox L 100 mg | 1200 | — | 14.4 | — | — | — | 204 | 118.2 |
| Amlexanox CP 100 mg | 1200 | — | 14.4 | 240 | — | 240 | 60 | 143.0 |
| Amlexanox M 100 mg | 1000 | — | 12 | — | 720 | 240 | — | 197.2 |

Example 14

Chemical Stability of Amlexanox Sodium Salt Solution 20 mg of crystalline Amlexanox sodium salt was dissolved in a clear glass test tube in 2 mL of Tris buffer, pH 7.2. For each of the stabilizing compounds listed in the Table below, 0.05 molar equivalent of the compound was added to the solution, mixed until dissolved, and left under ambient light, and with access to the air. Concentration of Amlexanox in the sample was determined by HPLC right after preparation, and after 72 hours. The chemical stability of Amlexanox was evaluated by comparison of area under the peak of amlexanox from the two analyses. The results are listed in the table below.

| Compound | Retained Amlexnox [%] |
|---|---|
| None | 93.8 |
| Maltol | 99.6 |
| Ascorbic acid | 99.5 |
| Caffeine | 96.8 |
| Glucose | 96.5 |
| Methyl 4-hydroxybenzoate | 93.1 |
| Propyl galate | 99.7 |

Example 15

Preparation of water-soluble 2-amino-7-chloro-1-azaxanthone-3-carboxylic acid sodium salt 2-amino-7-chloro-1-azaxanthone-3-carboxylic acid was solubilized in NaOH, pH of solution was adjusted to 7.6-7.8 with 1 M Tris, pH 7.4 and desirable volume was adjusted with autoclaved distilled water. Final concentration of NaOH was equimolar to concentration of 2-amino-7-chloro-1-azaxanthone-3-carboxylic acid. Specifically, to make 20 ml of 20 mg/ml solution, 400 mg of 2-amino-7-chloro-1-azaxanthone-3-carboxylic acid were dissolved in 10 ml of 132 mM NaOH and then 5.2 ml of 1 M Tris, pH 7.4 and 4.8 ml of water were added. Solution was sterilized through 0.2 micrometer filter.

Example 16

Preparation of instantly soluble 2-amino-7-chloro-1-azaxanthone-3-carboxylic acid formulation with meglumine The compositions of instantly soluble 2-amino-7-chloro-1-azaxanthone-3-carboxylic acid formulations with meglumine are listed in the Table below. The compositions were prepared by mixing of weighted amounts of dry powders for 90 minutes in a planetary mixer. Dissolution of the formulation was tested by placing the 85 mg of powder formulation in 5 mL water. The solution becomes clear in less than 2 minutes.

| Formulation | 2-amino-7-chloro-1-azaxanthone-3-carboxylic acid [mg] | Meglumine [mg] | Strawbery flavor* [mg] |
|---|---|---|---|
| F6 oral and for injection | 1000 | 700 | — |
| F7 oral | 1000 | 700 | 5 |

Example 17

Preparation of 2-amino-7-chloro-1-azaxanthone-3-carboxylic acid tablets

The compositions of the tablets are listed in the Table below. The prescribed amounts of 2-amino-7-chloro-1-azaxanthone-3-carboxylic acid, and the prescribed amounts of the excipients, in milligrams, were mixed in a planetary mixer for 60 minutes. The 20 mg and 100 mg tablets were prepared using a 7 mm dye. The 250 mg tablets were prepared using 13 mm dye. The tablets were pressed with 5000 lb pressure using Carver Hydraulic Laboratory Press.

| Dose | 2-amino-7-chloro-1-azaxanthone-3-carboxylic acid parts by weight | Pruve parts by weight | Carbopol 971P parts by weight | Meglumine parts by weight | Cellulose crys. parts by weight | Lactose parts by weight | Tablet weight (mg) |
|---|---|---|---|---|---|---|---|
| 20 mg  | 400  | 10   | —   | —   | 590  | —  | 50    |
| 250 mg | 5000 | 100  | —   | —   | 4900 | —  | 500   |
| 100 mg | 1200 | 14.4 | 240 | —   | 240  | 60 | 143.0 |
| 100 mg | 1000 | 12   | —   | 700 | 240  | —  | 195.2 |

Example 18

Preparation of water-soluble 2-amino-7,9-dimethyl-1-azaxanthone-3-carboxylic acid sodium salt 2-amino-7,9-dimethyl-1-azaxanthone-3-carboxylic acid was solubilized in NaOH, pH of solution was adjusted to 7.6-7.8 with 1 M Tris, pH 7.4 and desirable volume was adjusted with autoclaved distilled water. Final concentration of NaOH was equimolar to concentration of 2-amino-7,9-dimethyl-1-azaxanthone-3-carboxylic acid. Specifically, to make 20 ml of 20 mg/ml solution, 400 mg of 2-amino-7,9-dimethyl-1-azaxanthone-3-carboxylic acid were dissolved in 10 ml of 132 mM NaOH and then 5.2 ml of 1 M Tris, pH 7.4 and 4.8 ml of water were added. Solution was sterilized through 0.2 micrometer filter.

Example 19

Preparation of instantly soluble 2-amino-7,9-dimethyl-1-azaxanthone-3-carboxylic acid formulation with meglumine The compositions of instantly soluble 2-amino-7,9-dimethyl-1-azaxanthone-3-carboxylic acid formulations with meglumine are listed in the Table below. The compositions were prepared by mixing of weighted amounts of dry powders for 90 minutes in a planetary mixer. Dissolution of the formulation was tested by placing the 85 mg of powder formulation in 5 mL water. The solution becomes clear in less than 2 minutes.

| Formulation | 2-amino-7,9-dimethyl-1-azaxanthone-3-carboxylic acid [mg] | Meglumine [mg] | Strawbery flavor* [mg] |
|---|---|---|---|
| F8 oral and for injection | 1000 | 700 | — |
| F9 oral | 1000 | 700 | 5 |

Example 20

Preparation of 2-amino-7,9-dimethyl-1-azaxanthone-3-carboxylic acid tablets

The compositions of the tablets are listed in the Table below. The prescribed amounts of 2-amino-7,9-dimethyl-1-azaxanthone-3-carboxylic acid, and the prescribed amounts of the excipients, in milligrams, were mixed in a planetary mixer for 60 minutes. The 20 mg and 100 mg tablets were prepared using a 7 mm dye. The 250 mg tablets were prepared using 13 mm dye. The tablets were pressed with 5000 lb pressure using Carver Hydraulic Laboratory Press.

| Dose | 2-amino-7,9-dimethyl-1-azaxanthone-3-carboxylic acid parts by weight | Pruve parts by weight | Carbopol 971P parts by weight | Meglumine parts by weight | Cellulose crys. parts by weight | Lactose parts by weight | Tablet weight (mg) |
|---|---|---|---|---|---|---|---|
| 20 mg  | 400  | 10   | —   | —   | 590  | —  | 50    |
| 250 mg | 5000 | 100  | —   | —   | 4900 | —  | 500   |
| 100 mg | 1200 | 14.4 | 240 | —   | 240  | 60 | 143.0 |
| 100 mg | 1000 | 12   | —   | 700 | 240  | —  | 195.2 |

Example 21

Bioavailability of Amlexanox Acid and Amlexanox Sodium Salt in Normal Rats

Animals

Female CD rats (from 200 to 250 g body weight) were obtained from Charles River Canada Inc. (St. Constant, Quebec, Canada). The animals were kept 4 per cage with an air filter cover under light (12 h light/dark cycle, light on at 06 h 00) and temperature (22°±1° C.)-controlled environment. All manipulations with the animals were performed under a sterilized laminar hood. The animals had ad libitum access to Purina rat chow (Pro Lab PMH 4018, Trademark of Agway, Syracuse, N.Y.) and water. The animal studies were conducted according to the "Guidelines for Care and Use of Experimental Animals".

Dosing and Sampling

For Amlexanox salt the dosing solution was prepared by dissolving 20 mg of Amlexanox in equi-molar NaOH solution and then, equilibrated with 1M Tris-HCl pH 7.4. For Amlexanox acid the dosing solution was prepared by simple suspending 20 mg of Amlexanox in 1% methyl cellulose in water.

Amlexanox dosing solution (20 mg/mL) was administered i.v. and orally in normal rats (four animals in each group) at doses of 10, 25, 50, 100 and 200 mg/kg. After various time intervals (30 min and 1, 3, 6, 10 and 24 h) post-injection, blood was collected from eye vein of animals. Then, blood was immediately centrifuged, and plasma was separated. The plasma samples were immediately frozen in dry ice and stored at −80° C. until further use.

Extraction Procedure

The defrosted plasma samples were centrifuged at 2000 g for 5 min, and aliquots (10 μL) of each sample were transferred into 1.5-ml plastic tubes. The samples were diluted with phosphate buttered saline (PBS) in various amounts of times and aliquots of 100 μL were transferred into the other 1.5-ml plastic tubes. The samples were extracted with 1 mL of 100% acetonitrile for 10 min on 180° rotator. Then, the tubes were centrifuged at 10,000 g for 15 min.

The supernatant was separated to glass tubes and evaporated in a stream of nitrogen at −40° C. until dryness. The dried samples were kept at −20° C. until HPLC analysis. The samples were reconstituted in 100 μL of mobile phase analyze before analyze by HPLC.

HPLC Analysis

The samples were analysed by HPLC using 250×4.6 mm, Phenomenex C18 Luna, 5 micron column, 1 mL/min flow rate of mobile phase 73% of 25 mM sodium phosphate pH 7.5 and 27% acetonitrile; fluorescent deyection $\lambda_{excitation}$=348 nm, $\lambda_{emission}$=404 nm.

The concentrations of Amlexanox in samples were determined by comparison with calibration curve obtained from spiked rat plasma samples using the same analytical method. The areas under the curves (AUC) of Amlexanox were calculated by trapezoidal method.

Main pharmacokinetic parameters of Amlexanox and bioavailability of Amlexanox salt and acid are shown in Tables below.

TABLE

Amlexanox (salt) I.V. administration

| Dose mg/kg | AUC (μg·h)/mL | $C_{max}$ μg/mL | $t_{1/2}$ h | MRT h | CL L/(kg·h) | $V_{ss}$ L/kg |
|---|---|---|---|---|---|---|
| 10 | 3.3 | 4.5 | 0.52 | 0.75 | 3.0 | 2.26 |
| 25 | 47.0 | 33.4 | 1.29 | 1.87 | 0.53 | 0.99 |
| 50 | 216.8 | 165.1 | 0.69 | 1.05 | 0.1 | 0.1 |
| 100 | 398.4 | 216.3 | 0.75 | 1.14 | 0.13 | 0.14 |
| 200 | 739.0 | 466.0 | 1.31 | 1.89 | 0.27 | 0.51 |

TABLE

Amlexanox (salt) oral administration

| Dose mg/kg | AUC (μg·h)/mL | $C_{max}$ μg/mL | $t_{1/2}$ h | MRT h | CL L/(kg·h) | $V_{ss}$ L/kg |
|---|---|---|---|---|---|---|
| 10 | 1.04 | 0.19 | 5.76 | 8.29 | 9.6 | 79.8 |
| 25 | 2.2 | 0.55 | 5.33 | 7.71 | 11.4 | 87.7 |
| 50 | 4.47 | 1.59 | 5.04 | 7.28 | 11.2 | 81.4 |
| 100 | 41.15 | 19.8 | 1.42 | 2.05 | 2.43 | 4.99 |
| 200 | 200.5 | 95.2 | 1.23 | 1.77 | 0.5 | 0.89 |

TABLE

Amlexanox (acid) oral administration

| Dose mg/kg | AUC (μg·h)/mL | $C_{max}$ μg/mL | $t_{1/2}$ h | MRT h | CL L/(kg·h) | $V_{ss}$ L/kg |
|---|---|---|---|---|---|---|
| 10 | 1.05 | 0.37 | 4.36 | 6.28 | 9.50 | 59.8 |
| 25 | 1.38 | 0.26 | 7.81 | 11.26 | 18.10 | 204 |
| 50 | 2.38 | 0.58 | 5.84 | 8.43 | 21.01 | 177.2 |
| 100 | 8.83 | 1.17 | 6.04 | 8.70 | 11.30 | 98.5 |
| 200 | 18.6 | 7.0 | 3.68 | 5.32 | 5.37 | 28.5 |

TABLE

Bioavailability of Amlexanox salt and acid for oral administration

| Dose mg/kg | Amlexanox salt, % | Amlexanox acid, % |
|---|---|---|
| 10 | 31.2 | 31.5 |
| 25 | 4.7 | 2.9 |
| 50 | 2.1 | 1.1 |
| 100 | 10.3 | 2.2 |
| 200 | 27.1 | 2.5 |

Example 22

Pharmacokinetics of Amlexanox Acid and Amlexanox Sodium Salt in Normal Dogs

Animals

Experiments were performed in 6 male Beagle dogs (*Canis familiaris*) (from 8 to 14 kg body weight, 2 to 3 years of age). The animals had ad libitum access to tap water. Commercial dog chow was provided to the animals once daily during a 2-hour feeding period.

Methods

Dosing solution of amlexanox salt was prepared by simple dissolving of amlexanox salt in water. Dosing solution of amlexanox acid was prepared suspending of amlexanox acid in 0.5% methyl cellulose.

Amlexanox acid and Na salt forms were orally administered by gavage in dogs (three animals in each group) at doses of 10 mg/kg. Amlexanox tablets L and CP, prepared according to Example 13, were administered to dogs orally at doses of 10 mg/kg. After various time intervals (pre-dose, 15, 30 min and 1, 2, 3, 6, 8, 12, 24 and 48 h) post-injection, blood was collected from the jugular vein of animals. Then, blood was immediately centrifuged, and plasma was separated. The plasma samples were immediately frozen in dry ice and stored at −80° C. until further use.

Extraction Procedure

The defrosted plasma samples were centrifuged at 2000 g for 5 min, and aliquots (10 μL) of each sample were transferred into 1.5-ml plastic tubes. The samples were diluted with PBS in various amounts of times and aliquots of 100 μL were transferred into the other 1.5-ml plastic tubes. The samples were extracted with 1 mL of 100% acetonitrile for 10 min on 180° rotator. Then, the tubes were centrifuged at 10,000 g for 15 min.

The supernatant was separated to glass tubes and evaporated in a stream of nitrogen at −40° C. until dryness. The dried samples were kept at −20° C. until HPLC analysis. The samples were reconstituted in 100 μL of mobile phase analyze before analyze by HPLC.

HPLC Analysis

The samples were analysed by HPLC using 250×4.6 mm, Phenomenex C18 Luna, 5 micron column, 1 mL/min flow rate of mobile phase 73% of 25 mM sodium phosphate pH 7.5 and 27% acetonitrile; fluorescent deyection $\lambda_{excitation}$=348 nm, $\lambda_{emission}$=404 nm.

The concentrations of amlexanox in samples were determined by comparison with calibration curve obtained from spiked dog plasma samples using the same analytical method. The areas under the curves (AUC) of amlexanox were calculated by trapezoidal method. Main pharmacokinetic parameters of amlexanox are shown in the Table below.

TABLE

Main PK parameters of Amlexanox acid and Na salt after oral administration at dose of 10 mg/kg calculated by using trapezoidal method for plasma of normal dogs

| Amlexanox | AUC (μg·h)/mL | $C_{max}$ μg/mL | $t_{1/2}$ h | MRT h | CL L/(kg·h) | $V_{ss}$ L/kg |
|---|---|---|---|---|---|---|
| Acid | 7.6 | 3.4 | 2.3 | 3.3 | 1.3 | 4.3 |
| Na Salt | 29.0 | 10.7 | 1.8 | 2.5 | 0.3 | 0.9 |
| Tablet L | 12.9 | 6.03 | 0.5 | 1.9 | 2.7 | 0.8 |
| Tablet CP | 7.6 | 1.3 | 3.0 | 2.8 | 4.0 | 1.3 |

Example 23

Pharmacokinetics and Bioavailability of Amlexanox Sodium Salt and Amlexanox Meglumine Formulation in Normal Mice Animals Female C57BL/6 mice were used at 6 to 7 weeks of age. The animals were given food (Purina mouse chow, Pro Lab PMH 4018, Trademark of Agway, Syracuse, N.Y., USA) and water ad libitum. The mice were kept at five per cage under light (12 h light/dark cycle) and temperature (22±1° C.) controlled environment. The animal studies were conducted according to the "Guidelines for Care and Use of Experimental Animals".

Dosing and Sampling

Amlexanox sodium salt dosing solutions for oral administration were prepared by dissolving amlexanox sodium salt, prepared according to Example 10, in distilled water. amlexanox sodium salt dosing solutions for i.v. administration were prepared by dissolving amlexanox sodium salt, prepared according to Example 10, in isotonic solution (0.9% NaCl). Amlexanox meglumine formulation dosing solutions for oral administration were prepared by dissolving amlexanox meglumine formulation F1, prepared according to Example 12, in distilled water. Amlexanox meglumine formulation dosing solutions for i.v. administration were prepared by dissolving amlexanox meglumine formulation F1, prepared according to Example 13, in isotonic solution (0.9% NaCl). 1 mg/mL solution of amlexanox was used for dosing 10 mg/kg, and 10 mg/mL solution was used for dosing 100 mg/kg.

Amlexanox-X dosing solutions were administered i.v. and orally in normal mice (four animals per each time point). After various time intervals (15, 30 min and 1, 3, 6 and 8 h for Amlexanox-X Na salt and 15, 30 min, 1, 2 and 6 h for Amlexanox-X+MG) post-injection, blood and major organs (liver, kidney, lung and brain) were collected. Then, blood was immediately centrifuged, and plasma was separated. The plasma and tissue samples were immediately frozen in dry ice and stored at −80° C. until further use.

Extraction Procedure

The defrosted plasma samples were centrifuged at 2000 g for 5 min, and aliquots (10 μL) of each sample were transferred into 1.5-ml plastic tubes. The samples were diluted with PBS in various amounts of times and aliquots of 100 μL were transferred into the other 1.5-ml plastic tubes. The samples were extracted with 1 mL of 100% acetonitrile for 10 min on 180° rotator. Then, the tubes were centrifuged at 10,000 g for 15 min.

The supernatant was separated to glass tubes and evaporated in a stream of nitrogen at −40° C. until dryness. The dried samples were kept at −20° C. until HPLC analysis. The samples were reconstituted in 100 μL of mobile phase analyze before analyze by HPLC.

HPLC Analysis

The samples were analysed by HPLC using 250×4.6 mm, Phenomenex C18 Luna, 5 micron column, 1 mL/min flow rate of mobile phase 73% of 25 mM sodium phosphate pH 7.5 and 27% acetonitrile; fluorescent deyection $\lambda_{excitation}$=348 nm, $\lambda_{emission}$=404 nm.

The concentrations of amlexanox in samples were determined by comparison with calibration curve obtained from spiked mouse plasma samples using the same analytical method. The areas under the curves (AUC) of amlexanox were calculated by trapezoidal method. Main pharmacokinetic parameters of amlexanox and bioavailability if amlexanox Na salt and amlexanox with meglumine formulation are shown in Tables below.

TABLE

Main PK parameters of Amlexanox Na salt after oral administration at doses of 10 and 100 mg/kg calculated by using trapezoidal method for plasma of normal mice

| Dose mg/kg | AUC (μg·h)/mL | $C_{max}$ μg/mL | $t_{1/2}$ h | MRT h | CL L/(kg·h) | $V_{ss}$ L/kg |
|---|---|---|---|---|---|---|
| 10 | 19.3 | 17.6 | 1.1 | 1.6 | 0.5 | 0.8 |
| 100 | 301.5 | 206.3 | 1.5 | 2.2 | 0.03 | 0.07 |

TABLE

Main PK parameters of Amlexanox Na salt after i.v. administration at doses of 10 and 100 mg/kg calculated by using trapezoidal method for plasma of normal mice

| Dose mg/kg | AUC (μg·h)/mL | $C_{max}$ μg/mL | $t_{1/2}$ h | MRT h | CL L/(kg·h) | $V_{ss}$ L/kg |
|---|---|---|---|---|---|---|
| 10 | 31.3 | 55.7 | 0.4 | 0.5 | 0.3 | 0.2 |
| 100 | 733.7 | 589.6 | 0.8 | 1.2 | 0.01 | 0.02 |

TABLE

Main PK parameters of Amlexanox + Meglumine formulation after oral and i.v. administration at dose of 100 mg/kg calculated by using trapezoidal method for plasma of normal mice

| Amlexanox + MG Adm. | AUC (µg · h)/mL | $C_{max}$ µg/mL | $t_{1/2}$ h | MRT h | CL L/(kg · h) | $V_{ss}$ L/kg |
|---|---|---|---|---|---|---|
| Oral | 225.9 | 112.6 | 1.03 | 1.5 | 0.04 | 0.07 |
| I.V. | 592.1 | 528.1 | 0.5 | 0.7 | 0.02 | 0.01 |

TABLE

Bioavailability of Amlexanox sodium salt and Amlexanox meglumine formulation (MG) for oral administration

| Dose mg/kg | Amlexanox salt, % | Amlexanox MG, % |
|---|---|---|
| 10 | 61.7 | — |
| 100 | 41.1 | 38.2 |

Example 24

Anti-Metastatic Effect of Amlexanox in CSML100 (Murine Mammary Carcinoma) Experimental Metastasis Models Amlexanox solution for injections was prepared according to the Example 4. CSML100 cells were inoculated intravenously in 26 female A/J mice (6-7 weeks old). Animals were then divided randomly into two groups: 1) untreated control (n=16, saline) and 2) Amlexanox treated (n=10, 100 mg/kg/day, i.v.; 10 daily injections). The control group received i.v. injections with 5 ml/kg (volume/body weight) of saline, while Amlexanox was administered intravenously daily with a dose of 100 mg/kg in a volume of 5 ml/kg. Treatment was started on the day following the day of tumor cell implantation and continued for 10 consecutive days. The animal body weight was recorded as an index of treatment toxicity during the experiment. From the day 10 after cell implantation, one animal in the control group was sacrificed every day to monitor the metastasis development. All remaining animals were sacrificed on the day 18 for routine metastasis inspection. Although all organs were routinely screened, metastatic formation was only found in the lungs. The metastatic colonies on the organ surface were enumerated immediately following the removal of the organ.

Data in the Table demonstrate metastases formation in mice inoculated i.v. with CSML100 cells. A maximum body weight loss in treated group was less than 10%. The data are expressed as mean±SEM for the number of metastatic sites on the lung surface.

| Animal group | Average of lung metastasis number per animal (sample number) | Treated/control × 100% |
|---|---|---|
| Control | 38.8 ± 7.3 (9) | — |
| Treated | 18.8 ± 2.3 (9) | 48.5% |

Example 25

Anti-Metastatic Effect of Oral Amlexanox Alone or in Combinations with topotecan (TPT), doxorubicin (Dox) or paclitaxel (PTX) in S100A4-Positive Lung Metastasis Tumor Model Amlexanox solution for injections was prepared according to the Example 4. CSML100 cells ($1.2 \times 10^5$ cells per animal) were inoculated intravenously in 85 female A/J mice (6-7 weeks) obtained from The Jackson Laboratory (Maine, USA). The animals were then divided randomly into 9 groups (n=9 except for control group): 1) intact control (n=13, saline); 2) Amlexanox (i.v. 100 mg/kg); 3) Amlexanox (p.o. 200 mg/kg); 4) TPT (i.v. 3 mg/kg); 5) Amlexanox (p.o. 200 mg/kg)+TPT (i.v. 3 mg/kg); 6) Dox (i.v. 3 mg/kg); 7) Amlexanox (p.o. 200 mg/kg)+Dox (i.v. 3 mg/kg); 8) PTX (i.v. 10 mg/kg), and 9) Amlexanox (p.o. 200 mg/kg)+PTX (i.v. 10 mg/kg).

Intact control received oral administration with 10 ml/kg (volume/body weight) of saline while Amlexanox was administered orally and daily in a dose of 200 mg/kg in volume of 10 ml/kg or intravenously and daily in a dose of 100 mg/kg (5 ml/kg). The treatments were started on the day following the tumor cell implantation and continued for 10 consecutive days. Cytotoxic drugs, TPT, Dox or PTX, were administrated intravenously on day 1, 4, and 7 after tumor implantation. The animal body weight was recorded as an index of treatment toxicity during the experiment.

The data in Table show metastasis development. The data are expressed as mean±SEM for the number of metastatic sites on the lung surface.

| Treatment Groups | Treatment Schedule (injection) | Lung Metastasis Number per Animal |
|---|---|---|
| 1. Control | — | 35.0 ± 6.04 |
| 2. Amlexanox (i.v. 100 mg/kg) | daily i.v. injection | 29.6 ± 3.89 |
| 3. Amlexanox (p.o. 200 mg/kg) | Daily p.o. administration | 26.2 ± 4.16 |
| 4. TPT (i.v. 3 mg/kg) | On day 1, 4 7 | 6.20 ± 1.32 |
| 5. Amlexanox (p.o. 200 mg/kg) + TPT (i.v. 3 mg/kg) | Daily p.o. adm On day 1, 4, 7 | 1.60 ± 0.62 |
| 6. Dox (i.v. 3 mg/kg) | On day 1, 4, 7 | 15.6 ± 2.66 |
| 7. Amlexanox (p.o. 200 mg/kg) + Dox (i.v. 3 mg/kg) | Daily p.o. adm On day 1, 4, 7 | 14.3 ± 3.92 |
| 8. PTX (i.v. 10 mg/kg) | On day 1, 4, 7 | 40.8 ± 9.48 |
| 9. Amlexanox (p.o. 200 mg/kg) + PTX (i.v. 10 mg/kg) | Daily p.o. adm On day 1, 4, 7 | 28.0 ± 4.67 |

Example 26

Anti-Metastatic Effect of Oral Amlexanox and its Combination with topotecan (TPT) in B16 Experimental Metastasis Model Amlexanox solution for injections was prepared according to the Example 4. B16F10/DX cell ($2.0 \times 10^5$ cells per animal) were inoculated intravenously in female C57BL//6 mice (6-7 weeks old) and animals were then divided randomly into 4 groups (n=9 except for control group): 1) intact control (n=12, saline); 2) Amlexanox (100 mg/kg, daily p.o. administration); 3) TPT (2.0 mg/kg i.v. administration on day 1, 4, and 7); 5) Amlexanox (daily p.o. 100 mg/kg)+TPT (i.v. 2.0 mg/kg on day 1, 4, and 7). Intact control received oral administration with 10 ml/kg (volume/body weight) of saline, while Amlexanox was administrated orally and daily with a dose of 100 mg/kg in a volume of 10 ml/kg. The treatments were started from the day following the tumor cell implantation until the end of the protocol. However, TPT was administrated intravenously only on day 1, 4, and 7 after tumor implantation. The animal body weight was recorded as an index of treatment toxicity during the experiment.

The data in Table show metastasis formation in the lung in the mice implanted with B16F10/DX cells. The data are expressed as mean±SEM for the number of metastatic sites on the lung surface.

| Group | Treatment schedule | Injection Volume (ml/kg) | Animals per group | Lung metastasis number per animal |
|---|---|---|---|---|
| 1. Control | Daily p.o. (saline) | 10 | 9 | 134.3 ± 25.8 |
| 2. Amlexanox (100 mg/kg) | Daily p.o. | 10 | 9 | 71.3 ± 15.5 |
| 3. TPT (2.0 mg/kg) | i.v. on day 1, 4, and 7 | 10 | 9 | 88.0 ± 8.79 |
| 4. Amlexanox (100 mg/kg) + TPT (2.0 mg/kg) | Daily p.o. + i.v. on day 1, 4, and 7 | 10 | 9 | 61.0 ± 5.0 |

Example 27

Anti-Cancer Activity of Amlexanox in the Spontaneous Metastasis Model in Mice

Amlexanox solution for injections was prepared according to the Example 4. CSML100 cells ($2.0 \times 10^6$ cells per animal) were inoculated subcutaneously to female A/J mice (6-7 weeks old). The animals were then divided randomly into 2 groups (n=9): Intact control (saline) and Amlexanox treated (100 mg/kg, daily i.v. injection for 10 consecutive days). The treatment started from the day following the tumor implantation. The measurement of tumor size was performed since day 11. On day 24, the tumors were surgically removed. The lung metastasis development was analyzed 40 days after the tumor resection.

The data in Table show spontaneous lung metastasis formation in this tumor model. The data are expressed as mean±SEM for the number of metastatic sites on the lung surface.

What is claimed:

1. A method of retarding the metastasis of an epithelial or mesenchymal tumor which expresses S100 human $Ca^{2+}$-binding protein comprising administering to a human patient having said tumor, a compound selected from the group consisting of 2-amino-7-isopropyl-1-azaxanthone-3-carboxylic acid, pharmacologically acceptable salts thereof and esters thereof; with said compound being administered to said patient in an effective amount to retard the metastasis of said tumors.

2. The method of claim 1 wherein said tumor is selected from the group consisting of tumors of the breast, skin, colon, lung, bladder, pancreas, esophagus, stomach or oral cavity.

3. The method of claim 2 wherein said tumor is a tumor of the breast or skin.

4. The method of claim 1 wherein said compound is administered orally at daily dosages of from about 3 to 60 mg/kg of body weight.

5. The method of claim 2 wherein said compound is administered in an oral unit dosage form containing from about 20 to 600 mg of the compound.

6. The method of claim 5 wherein said oral unit dosage form is a tablet or capsule.

7. The method of claim 1 wherein the compound is administered to a patient as a meglumine salt.

8. The method of claim 7 wherein the compound is administered by injection of said salt.

9. The method of claim 1 wherein said tumor is a tumor of the breast.

10. The method of claim 1 wherein said tumor is a tumor of the colon.

11. A method for treating malignancies in patients where said malignancies consist of epithelial or mesenchymal tumors which express S100 human $Ca^{2+}$-binding protein comprising (a) treating said tumors in said patient by reducing the size of or by removal of said tumor and, (b) in conjunction with said treatment, administering to said patient, to retard the metastasis of said tumor, a compound selected from or the group consisting of 2-amino-7-isopropyl-1-azaxanthone-3-carboxylic acid, or pharmacologically acceptable salts or esters thereof; with said compound being administered to said patient in an effective amount to retard the metastasis of said tumors.

12. The method of claim 11 wherein said reduction or removal of said tumor is by chemotherapy, surgery or radiation.

13. The method of claim 11 wherein said tumor is selected from the group consisting of tumors of the breast, skin, colon, lung, bladder, pancreas, esophagus, stomach or oral cavity.

| Animal group | Treatment | Subcutaneous tumor size on day 14, g | Lung metastasis number 40 days after s.c. tumor resection | Trial/control × 100% |
|---|---|---|---|---|
| Control | Saline (daily i.v., 10 ml/kg) | 0.06 ± 0.02 (n = 9) | 27.33 ± 12.0 (n = 6)* | — |
| Amlexanox | 100 mg/kg, i.v. daily injection for 10 days | 0.05 ± 0.02 (n = 10) | 1.00 ± 0.55 (n = 5)** | 96.3% |

*Three animals were dead due to resection operation. One did not have any lung metastasis since no subcutaneous tumor was formed in this animal.
**Four mice were dead due to the resection operation. One was excluded as a statistically valid exception (26 metastases).

14. The method of claim 13 wherein said compound is administered orally at daily dosages of from about 3 to 60 mg/kg of body weight.

15. The method of claim 14 wherein said compound is administered orally in a unit oral dosage form containing from about 20 mg to 600 mg of the compound.

16. The method of claim 11 wherein said tumor is a tumor of the breast and skin.

17. The method of claim 11 wherein said tumor is a tumor of the breast.

18. A method of treating patients who have had an epithelial or mesenchymal tumor which expresses S100 human $Ca^{2+}$-binding protein treated by reducing its size or by removal, comprising administering to said patient to retard the metastasis of said epithelial or mesenchymal tumor, a compound selected from the group consisting of 2-amino-7-isopropyl-1-azaxanthone-3-carboxylic acid, pharmacologically acceptable salts thereof and esters thereof; said compound being administered in an effective amount to retard the metastasis of said tumor.

19. The method of claim 18 wherein said reduction or removal of said tumor is by chemotherapy, surgery or radiation.

20. The method of claim 18 wherein said tumor is selected from the group consisting of tumors of the breast, skin, colon, lung, bladder, pancreas, esophagus, stomach and oral cavity.

21. The method of claim 18 wherein said compound is administered orally at daily dosages of from about 3 to 60 mg/kg of body weight.

22. The method of claim 18 wherein said compound is administered in an oral unit dosage form containing from 20 to 600 mg of the compound.

23. The method of claim 18 where said tumor is a tumor of the breast or skin.

24. The method of claim 18 wherein said tumor is a tumor of the breast.

25. The method of claim 2 wherein said tumor is a tumor of the pancreas.

26. The method of claim 13 wherein said tumor is a tumor of the pancreas.

27. The method of claim 20 wherein said tumor is a tumor of the pancreas.

* * * * *